US009265654B2

(12) United States Patent
Gallaher

(10) Patent No.: US 9,265,654 B2
(45) Date of Patent: Feb. 23, 2016

(54) COOLING ARTICLE OF CLOTHING AND METHOD OF USE FOR SAME

(76) Inventor: Steven H. Gallaher, Overland Park, KS (US)

(*) Notice: Subject to any disclaimer, the term of this patent is extended or adjusted under 35 U.S.C. 154(b) by 428 days.

(21) Appl. No.: 12/778,111

(22) Filed: May 11, 2010

(65) Prior Publication Data

US 2010/0286755 A1    Nov. 11, 2010

Related U.S. Application Data

(60) Provisional application No. 61/177,144, filed on May 11, 2009.

(51) Int. Cl.
*A61F 7/02* (2006.01)
*A61F 7/10* (2006.01)
*A41D 13/005* (2006.01)
*A61F 7/00* (2006.01)

(52) U.S. Cl.
CPC .............. *A61F 7/02* (2013.01); *A41D 13/0053* (2013.01); *A61F 2007/0018* (2013.01); *A61F 2007/0058* (2013.01); *A61F 2007/026* (2013.01); *A61F 2007/0214* (2013.01); *A61F 2007/0219* (2013.01); *A61F 2007/0234* (2013.01)

(58) Field of Classification Search
CPC .. A41D 13/0053; A41D 13/0056; A61F 7/02; A61F 2007/0018; A61F 2007/0214; A61F 2007/0234
USPC .......................................... 607/108, 112, 114
See application file for complete search history.

(56) References Cited

U.S. PATENT DOCUMENTS

| 594,209 A | 11/1897 | Mears |
|---|---|---|
| 1,803,393 A | 5/1931 | Jones |
| 2,460,269 A | 2/1949 | Appeldoom |
| 2,512,559 A | 6/1950 | Williams |
| 2,769,308 A | 11/1956 | Krasno |
| 2,875,447 A | 3/1959 | Goldmerstein |
| 3,017,888 A | 1/1962 | Weiner |
| 3,029,438 A | 4/1962 | Henschel |
| 3,079,765 A | 3/1963 | Vantine |
| 3,212,286 A | 10/1965 | Curtis |
| 3,296,819 A | 1/1967 | Gough |
| 3,429,138 A | 2/1969 | Goldmerstein |
| 3,610,323 A | 10/1971 | Troyer |
| 4,324,111 A * | 4/1982 | Edwards ................. 62/457.4 |
| 4,484,363 A | 11/1984 | Varanese |
| 4,580,408 A | 4/1986 | Stuebner |
| 4,718,429 A | 1/1988 | Smidt |
| 4,742,581 A | 5/1988 | Rosenthal |

(Continued)

*Primary Examiner* — Kaitlyn Smith
(74) *Attorney, Agent, or Firm* — Scott T. Griggs; Griggs Bergen LLP

(57) ABSTRACT

A cooling article of clothing and method for use of the same are disclosed for providing temporary cooling comfort to a human wearer. In one embodiment, sealed elongated envelopes are formed on the inside of a layer of the fabric, which may be fashioned into a vest or shirt. Each of the sealed elongated envelopes defines a volume for containing a predetermined amount of polyacrylamide material. Offset spacings are interleaved between the sealed elongated envelopes. A diffusion gradient is formed from the polyacrylamide material to the sealed elongated envelopes to the layer of fabric. A diffusion gradient provides for the transfer of water from the polyacrylamide material to the layer of fabric. Water within the layer of fabric is evaporated by way of airflow through the layer of fabric, thereby providing temporary cooling comfort to the human wearer.

9 Claims, 2 Drawing Sheets

(56) References Cited

U.S. PATENT DOCUMENTS

| | | | |
|---|---|---|---|
| 4,856,294 A | 8/1989 | Scaringe et al. | |
| 4,998,415 A | 3/1991 | Larsen | |
| 5,146,625 A | 9/1992 | Steele et al. | |
| 5,263,336 A | 11/1993 | Kuramarohit | |
| 5,305,471 A | 4/1994 | Steele et al. | |
| 5,415,222 A | 5/1995 | Colvin et al. | |
| 5,433,083 A | 7/1995 | Kuramarohit | |
| 5,438,707 A | 8/1995 | Horn | |
| 5,524,293 A | 6/1996 | Kung | |
| 5,606,746 A | 3/1997 | Shelton et al. | |
| 5,755,110 A * | 5/1998 | Silvas | 62/259.3 |
| 5,940,880 A | 8/1999 | Phillips | |
| 5,967,225 A | 10/1999 | Jenkins | |
| 6,009,713 A | 1/2000 | Horn | |
| 6,067,803 A * | 5/2000 | Wolsey et al. | 62/60 |
| 6,125,645 A | 10/2000 | Horn | |
| 6,134,714 A | 10/2000 | Uglene | |
| 6,185,742 B1 | 2/2001 | Doherty | |
| 6,185,744 B1 | 2/2001 | Poholski | |
| 6,189,149 B1 | 2/2001 | Allen | |
| 6,260,201 B1 | 7/2001 | Rankin | |
| 6,298,907 B1 | 10/2001 | Colvin et al. | |
| 6,354,099 B1 | 3/2002 | Bieberich | |
| 6,371,977 B1 | 4/2002 | Bumbarger et al. | |
| 6,473,910 B2 | 11/2002 | Creagan et al. | |
| 6,543,247 B2 | 4/2003 | Strauss | |
| 6,551,347 B1 | 4/2003 | Elkins | |
| 6,584,798 B2 | 7/2003 | Schegerin | |
| 6,601,404 B1 | 8/2003 | Roderick | |
| 6,755,852 B2 * | 6/2004 | Lachenbruch et al. | 607/114 |
| 6,855,410 B2 | 2/2005 | Buckley | |
| 6,874,332 B2 | 4/2005 | Forgach | |
| 6,901,608 B2 | 6/2005 | Szczesuil et al. | |
| 6,915,641 B2 | 7/2005 | Harvie | |
| 6,931,875 B1 | 8/2005 | Allen et al. | |
| 6,942,015 B1 | 9/2005 | Jenkins | |
| 6,962,600 B2 | 11/2005 | Lennox et al. | |
| 6,976,276 B2 | 12/2005 | Corbitt, Jr. | |
| 6,979,382 B2 | 12/2005 | Szczesuil et al. | |
| 6,993,930 B2 | 2/2006 | Blackstone | |
| 7,000,682 B2 | 2/2006 | Chambers | |
| 7,001,417 B2 | 2/2006 | Elkins | |
| 7,010,931 B2 | 3/2006 | Lee | |
| 7,048,976 B2 * | 5/2006 | Caceres et al. | 428/34.7 |
| 7,124,593 B2 | 10/2006 | Feher | |
| 7,373,969 B2 | 5/2008 | Chambers | |
| 7,437,883 B1 | 10/2008 | Baldal | |
| 7,472,560 B2 | 1/2009 | Karch et al. | |
| 7,509,692 B2 | 3/2009 | Elkins et al. | |
| 7,565,705 B2 | 7/2009 | Elkins et al. | |
| D599,529 S | 9/2009 | Simpson | |
| 7,698,905 B1 | 4/2010 | Carpenter et al. | |
| 2002/0069448 A1 * | 6/2002 | Appolonia | 2/102 |
| 2002/0092312 A1 * | 7/2002 | Head | 62/259.3 |
| 2003/0208831 A1 * | 11/2003 | Lazar et al. | 2/69 |
| 2004/0226077 A1 * | 11/2004 | Toth | 2/411 |
| 2005/0055753 A1 | 3/2005 | Horn | |
| 2007/0163027 A1 * | 7/2007 | Hamilton | 2/171 |
| 2007/0174949 A1 * | 8/2007 | Howells | 2/171 |
| 2007/0204808 A1 * | 9/2007 | Harada | 119/850 |
| 2008/0077210 A1 | 3/2008 | Horn | |
| 2008/0141434 A1 * | 6/2008 | Pringles et al. | 2/127 |
| 2009/0036960 A1 * | 2/2009 | Blair | 607/109 |
| 2009/0264969 A1 * | 10/2009 | Gammons | 607/104 |
| 2010/0011489 A1 * | 1/2010 | Goldmann et al. | 2/455 |
| 2010/0101253 A1 * | 4/2010 | Searle | 62/259.3 |
| 2011/0094012 A1 * | 4/2011 | Toth | 2/171.2 |
| 2012/0046720 A1 * | 2/2012 | Ishizaki | 607/114 |

* cited by examiner

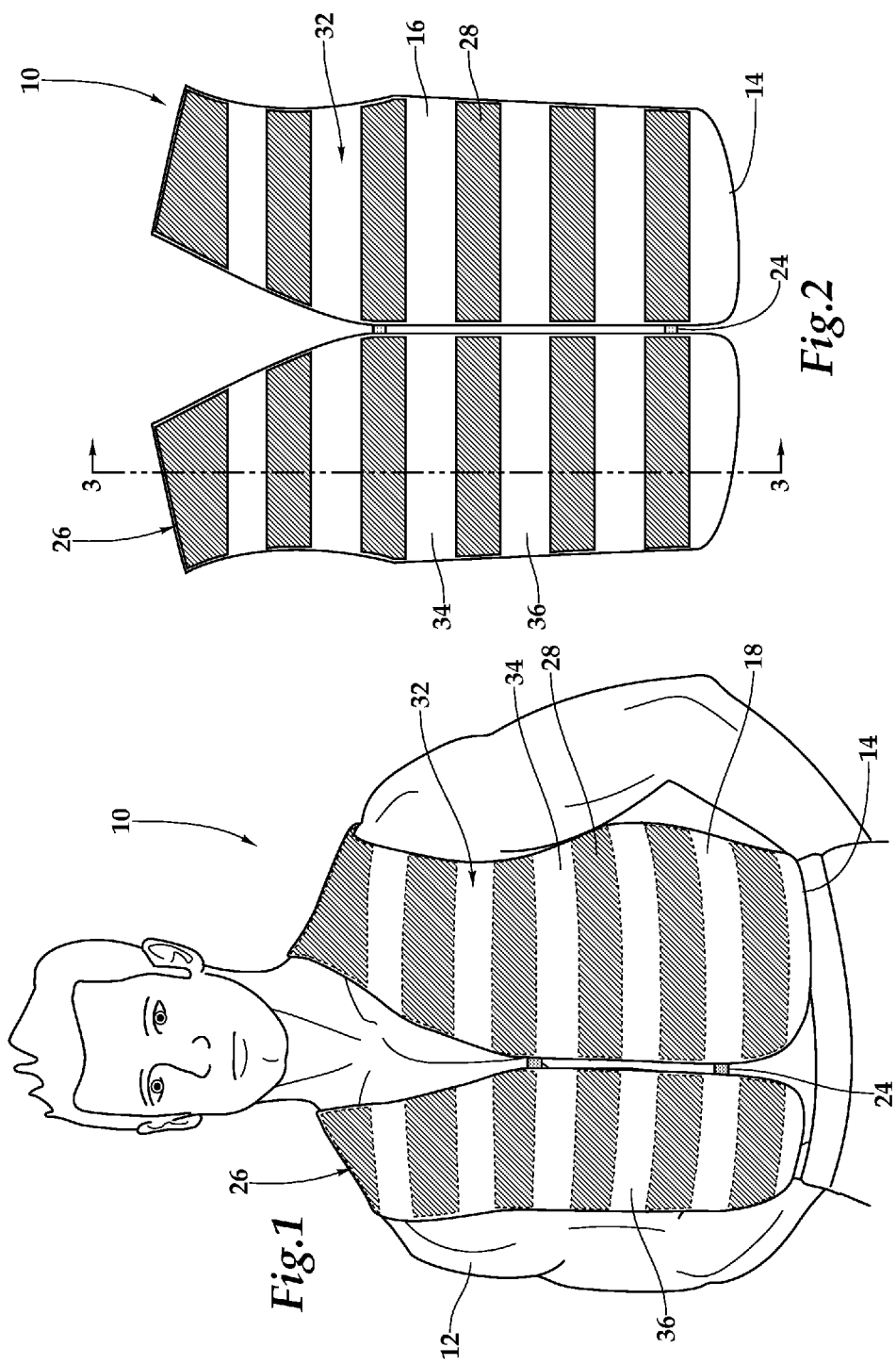

COOLING ARTICLE OF CLOTHING AND METHOD OF USE FOR SAME

PRIORITY STATEMENT & CROSS-REFERENCE TO RELATED APPLICATIONS

This application claims priority from U.S. Patent Application No. 61/177,144, entitled "Cooling Suit" and filed on May 11, 2009, in the name of Steven H. Gallaher, which is hereby incorporated by reference for all purposes.

TECHNICAL FIELD OF THE INVENTION

This invention relates, in general, to an article of clothing such as a vest and, in particular, to a cooling article of clothing that facilitates cooling a wearer in part by chemical action.

BACKGROUND OF THE INVENTION

Hyperthermia is an elevated body temperature due to failed thermoregulation. On a cold day, elevated body temperature can help the body maintain an optimal temperature. On a hot day, however, hyperthermia can occur when the body produces or absorbs more heat than can be dissipated. When the elevated body temperatures are sufficiently high, hyperthermia is a medical emergency and requires immediate treatment to prevent disability or death.

Hypothermia is typically experienced during physical exertion in a hot environment. Wearing a personal cooling system can prevent or mitigate the risks of hypothermia in such conditions. Important factors to the selection of a personal cooling system are weight and convenience. Existing personal cooling systems that utilize heat pumps or cold packs are encumbering, and particularly so, during physical exertion. There continues to be a need for advances in personal cooling systems.

SUMMARY OF THE INVENTION

A cooling article of clothing and method for use of the same are disclosed for providing temporary cooling comfort to a human wearer. In one embodiment, the cooling article of clothing has the form of an evaporative cooling vest. In particular, sealed elongated envelopes are formed on the inside of a layer of the fabric, which may be fashioned into a vest or shirt. Each of the sealed elongated envelopes defines a volume for containing a pre-determined amount of polyacrylamide material. Offset spacings are interleaved between the sealed elongated envelopes. A diffusion gradient is formed from the polyacrylamide material to the sealed elongated envelopes to the layer of fabric. A diffusion gradient provides for the transfer of water from the polyacrylamide material to the layer of fabric. Water within the layer of fabric is evaporated by way of airflow through the layer of fabric, thereby providing temporary cooling comfort to the human wearer. That is, the cooling article of clothing presented herein provides a light-weight, non-encumbering personal cooling system.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is a front perspective view of a human wearing one embodiment of a cooling article of clothing;

FIG. 2 is a rear elevation view of the inside of the frontside portion of the cooling article of clothing depicted in FIG. 1.

DETAILED DESCRIPTION OF THE INVENTION

Figure 3C:
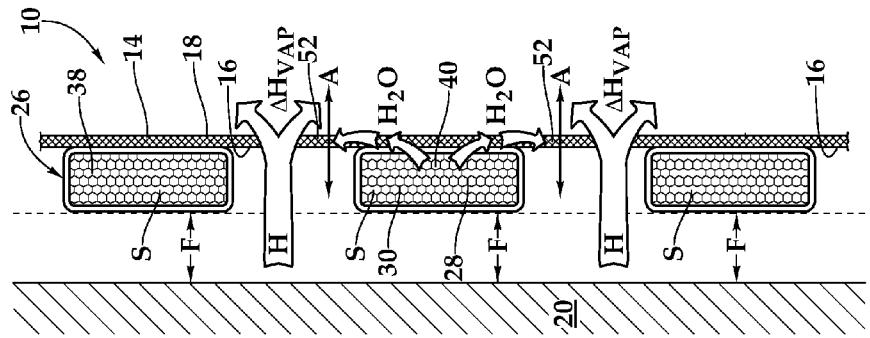
FIGS. 3A through 3C are cross-sectional views of the cooling article of clothing along line 3-3 in FIG. 2A to show an operational embodiment thereof.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIGS. 1 through 3A, therein is depicted a cooling article of clothing that is schematically illustrated and generally designated 10. The cooling article of clothing 10 provides temporary cooling comfort to a human wearer 12. It should be appreciated, however, that the cooling article of clothing 10 may be utilized with an animal as well. A layer of fabric 14 is provided having an inside 16 and an outside 18. The layer of fabric 14 may be porous and hydrophilic.

As shown, the layer of fabric 14 may be a light weave that includes stitching to be fashioned into an article of clothing, such as a vest or shirt or other torso covering garment to protect the major internal organs of the body from high ambient temperatures, for example. The layer of fabric 14 may have a stretchability sufficient to permit the cooling article of clothing 10 to fluctuate with respect to the body of the human wearer 12. By way of example, the layer of fabric 14 may be a performance fabric, e.g., fiber-based moisture management materials, that includes an effective fiber-based moisture management system. Such performance fabric is hydrophilic and has no or minimal expansion upon contact with water. An example of such a suitable fabric is COOLMAX® fabric by Koch Industries, Inc. (Wilmington, Del.).

Such a system can move perspiration away from the body, and through the fabric 14, where it can evaporate quickly, allowing the wearer 12 to feel cooler and more comfortable. As shown, the layer of fabric 14 is configured such that the inside 16 is positioned to contact human skin 20 and the outside presents a substantially continuous surface 22. As depicted, a closure mechanism 24, which, for example, may be a zipper, is furnished for selectively joining and separating the layer of fabric 14.

Sealed elongated envelopes 26 are formed on the inside 16 of the layer of the fabric 14. Each of the sealed elongated envelopes 26, including sealed elongated envelope 28, define a volume and is water absorbent or a mesh-like material. An end 30 of the sealed elongated envelope 28 may be formed by the layer of fabric 14 or, alternatively, formed independently thereof. Offset spacings 32, including offset spacings 34, 36, are interleaved between the elongated envelopes 26. It should be appreciated that although a particular pattern of sealed elongated envelopes 26 and offset spacings 32 is illustrated, other patterns and shapes are within the teachings presented herein. By way of example, the width of the materials may be adjusted to match the environment's airflow and humidity requirements.

A pre-determined amount of polyacrylamide material 38 is contained within each of the sealed elongated envelopes 26.

By way of example, a pre-determined amount of polyacrylamide material 40 is disposed within the sealed elongated envelope 28. The polyacrylamide material is porous and capable of absorbing water. Polyacrylamide (IUPAC poly (2-propenamide) or poly (1-carbamoylethylene)) is a polymer ($-CH_2CHCONH_2-$) formed from acrylamide subunits that can also be readily cross-linked. In the cross-linked form, the polyacrylamide material is highly water-absorbent, forming a soft gel or a crystal. It should be understood, that any water-absorbent polymer is also within the teachings presented herein.

With respect to the sealed elongated envelope 28 as an example of the sealed elongated envelopes 26, a diffusion gradient 50 is formed from the polyacrylamide material 40 to the sealed elongated envelope 28 to the layer of fabric 14. The diffusion gradient 50 provides for the transfer of water from the polyacrylamide material 40 to the layer of fabric 14. Water within the layer of fabric 14 is then evaporated by way of airflow through airflow passages of the layer of fabric, thereby providing temporary cooling comfort to the human wearer 12. It should be understood that although only the frontside of the cooling article of clothing 10 was described, the backside has a similar construction. Moreover, it should be understood that in one embodiment, the sealed elongated envelopes 26 are not continuous around the body. A strap may be located along the sides of the cooling article of clothing 10, such that the sealed elongated envelopes 26 are only cover the frontside and backside. It should be appreciated that other deviations of the placement of the sealed elongated envelopes 26 are within the teachings presented herein as well.

Figure 3B:
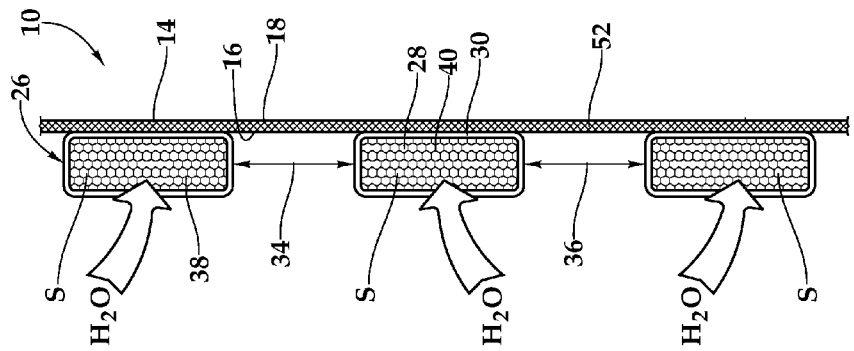
Figure 3A:
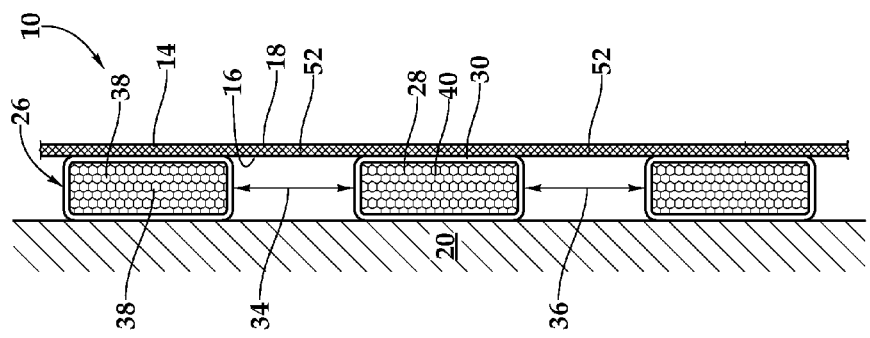

Referring to FIGS. 3B and 3C, in one operational embodiment, the cooling article of clothing 10 is soaked in water. As shown in FIG. 3B, the water ($H_2O$) is absorbed into the polyacrylamide material 40, which is saturated (S) in FIGS. 3B and 3C, as compared to FIG. 3A. The saturated polyacrylamide material 40 results in a moist sealed elongated envelope 30. The cooling article 10 is worn during strenuous physical activity in a harsh environment where it will be difficult for the body to self-thermoregulate. As previously discussed, a diffusion gradient 50 is established from the polyacrylamide material 40 through the moist sealed elongated envelope 28 to the layer of fabric 14.

With particular attention to FIG. 3C, during physical activity, water is transferred from the saturated polyacrylamide material 40 to the layer of fabric 14 along the diffusion gradient. In one embodiment, gravity may assist in this transfer. The water within the layer of fabric 14 is then evaporated by way of airflow (A) through the airflow passages 52 within the layer of fabric 14, thereby providing temporary cooling comfort to the human wearer 12. The enthalpy of vaporization ($\Delta H_{VAP}$) depicts the heat transfer from the skin 20 of the human wearer 12 to the environment. In this manner, the cooling article of clothing 10 permits a person or animal to exercise in hot weather without overheating.

More particularly, as previously alluded, the article of clothing 10 does not stay skin tight. Rather, the article of clothing fluctuates, as shown by the letter F, in and out of contact with the skin 20. In particular, the moist sealed elongated envelopes 26 contact the skin 20 of the body of the human wearer 12 and quickly absorbs heat (H), then the moist sealed elongated envelopes 26 swing away from the body of the wearer 12 to allow air and evaporation to occur. In one implementation, the fluctuation may be approximately ½ inch or more. The fluctuation F cools the sealed elongated envelopes 26, then the sealed elongated envelopes 26 swing back to the body of the human wearer 12.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A cooling article of clothing for providing temporary cooling comfort to a human wearer, the cooling article comprising:

a layer of fabric having an inside and an outside, the layer of fabric being porous and hydrophilic, the layer of fabric configured such that the inside is positioned to contact human skin, but for a plurality of sealed elongated envelopes, and the outside presents a substantially continuous surface;

the layer of fabric being fashioned as a torso covering garment for the human wearer;

the plurality of sealed elongated envelopes formed on the inside of the layer of the fabric, each of the plurality of sealed elongated envelopes defining a volume, each of the plurality of sealed elongated envelopes being water absorbent;

each of the plurality of sealed elongated envelopes being horizontal around the torso covering garment;

a plurality of horizontal offset spacings interleaved between the plurality of sealed elongated envelopes such that the space between adjacent sealed elongated envelopes of the plurality of sealed elongated envelopes consists of a horizontal stripped width of the layer of fabric in an alternating manner;

the plurality of sealed elongated envelopes and horizontal offset spacings providing at least three sealed elongated envelopes having a corresponding three horizontal offset spacings interleaved thereinbelow;

a pre-determined amount of polyacrylamide material contained within each of the sealed elongated envelopes, the polyacrylamide material being porous and capable of absorbing water;

each of the plurality of sealed elongated envelopes configured to fluctuate by swinging away from the body of the human wearer under the movement of the human wearer to allow air and evaporation along the entire adjacent horizontal stripped width of the layer of fabric;

a diffusion gradient formed from and including the polyacrylamide material to the plurality of sealed elongated envelopes to the layer of fabric, the diffusion gradient providing for the transfer of water from the polyacrylamide material to the layer of fabric, and the diffusion gradient utilizing gravity to furnish the water from the polyacrylamide material to the layer of fabric associated with the horizontal offset spacing interleaved thereinbelow;

wherein an enthalpy of vaporization occurs in substantially parallel horizontal planes along the entire adjacent horizontal stripped width of the layer of fabric as a result of the diffusion gradient and swinging away from the body of the human wearer, wherein water within the layer of fabric is evaporated by way of airflow through airflow passages within the layer of fabric, thereby providing temporary cooling comfort to the human wearer.

2. The cooling article as recited in claim 1, wherein the layer of fabric is fashioned into an article of clothing selected from the group consisting of vests and shirts.

3. The cooling article as recited in claim 1, wherein the layer of fabric comprises a stretchability sufficient to permit the article of clothing to fluctuate with respect to the body of the human wearer.

4. The cooling article as recited in claim 1, wherein the layer of fabric comprises stitching.

5. The cooling article as recited in claim 1, wherein the layer of fabric comprises a material selected from the group consisting of fiber-based moisture management materials and a hydrophilic material having minimal expansion upon contact with water.

6. The cooling article as recited in claim 1, further comprising a closure mechanism for selectively joining and separating the layer of fabric.

7. The cooling article as recited in claim 1, further comprising straps coupled to the layer of fabric.

8. A method for providing temporary cooling comfort to a human wearer, the method comprising:

providing a cooling article of clothing including a layer of fabric having an inside and an outside, a plurality of sealed elongated envelopes formed on the inside of the layer of the fabric, and a plurality of offset spacings interleaved in an alternating manner between the plurality of sealed elongated envelopes, each of the plurality of sealed elongated envelopes being horizontal around a torso covering garment, such that the space between adjacent sealed elongated envelopes of the plurality of sealed elongated envelopes consists of a horizontal stripped width of the layer of fabric, the plurality of sealed elongated envelopes and horizontal offset spacings providing at least three sealed elongated envelopes having a corresponding three horizontal offset spacings interleaved thereinbelow;

covering the human wearer with the layer of fabric which is fashioned as the torso covering garment for the human wearer;

containing a pre-determined amount of polyacrylamide material within each of the sealed elongated envelopes, the polyacrylamide material being porous and capable of absorbing water;

soaking the cooling article in water;

absorbing water into the polyacrylamide material;

wearing the cooling article such that the inside is positioned to contact human skin, but for the plurality of sealed elongated envelopes, and the outside presents a substantially continuous surface;

establishing a diffusion gradient from the polyacrylamide material to the plurality of sealed elongated envelopes to the layer of fabric, the diffusion gradient utilizing gravity to furnish the water from the polyacrylamide material to the layer of fabric associated with the horizontal offset spacing interleaved thereinbelow;

providing for the transfer of water from the polyacrylamide material to the layer of fabric;

fluctuating, responsive to movement from the human wearer, the layer of fabric in and out of contact with human skin, each of the plurality of sealed elongated envelopes configured to fluctuate by swinging away from the body of the human wearer under the movement of the human wearer to allow air and evaporation along the entire adjacent horizontal stripped width of the layer of fabric;

evaporating water within the layer of fabric by way of airflow through airflow passages within the layer of fabric;

causing an enthalpy of vaporization to occur in substantially parallel horizontal planes along the entire adjacent horizontal stripped width of the layer of fabric as a result of the diffusion gradient and swinging away from the body of the human wearer; and providing temporary cooling comfort to the human wearer.

9. The method as recited in claim 8, wherein providing a cooling article of clothing further comprises selecting the cooling article from the group consisting of vests and shirts.

* * * * *